US00PP08062P

United States Patent [19]

Ackerman

[11] Patent Number: Plant 8,062

[45] Date of Patent: Dec. 15, 1992

[54] RASPBERRY PLANT NAMED PSI-R86.745

[75] Inventor: Stephen M. Ackerman, Salinas, Calif.

[73] Assignees: Plant Sciences, Inc.; Coast Cooling, Inc., both of Watsonville, Calif.

[21] Appl. No.: 634,331

[22] Filed: Dec. 26, 1990

[51] Int. Cl.[5] ..... A01H 5/00

[52] U.S. Cl. ..... Plt./46.2

[58] Field of Search ..... Plt./46

[56] References Cited

U.S. PATENT DOCUMENTS

P.P. 113 11/1934 Curtis ..... Plt. 46

P.P. 3,717 5/1975 Hagerstrom ..... Plt. 46

P.P. 7,625 8/1991 Dixon ..... Plt. 46

*Primary Examiner*—James R. Feyrer

*Attorney, Agent, or Firm*—Christie, Parker & Hale

[57] ABSTRACT

A new and distinct everbearing golden raspberry variety named "PSI-R86.745" which is capable of producing fruit on first year primocanes, and on floricanes and primocanes in subsequent years. The new variety is characterized by relatively large fruit size, virtually thornless nature, and distinct color contrast between mature and immature foliage. The variety is also distinguishable by its tall unbranched primocane growth.

5 Drawing Sheets

BACKGROUND OF THE NEW CULTIVAR

This new variety of raspberry resulted from a breeding program jointly sponsored by Plant Sciences, Inc. and Coast Cooling, Inc., both of Watsonville, Calif., with the goal of developing new and distinct raspberry varieties. It originated from a cross of parents hereinafter described and was discovered as a chance seedling in a controlled breeding plot in Watsonville, Calif. The seedling was grown and asexually propagated by suckers during spring and summer seasons, also in Watsonville, Calif. After being selected, clones of the new variety, were further asexually propagated and extensively tested over two years in Watsonville, Calif. This propagation and reproduction has demonstrated that the combination of characteristics disclosed herein for the new variety are fixed and retained true to type through successive generations of asexual reproduction.

SUMMARY OF THE INVENTION

The present invention relates to a new and distinct everbearing golden raspberry variety. The varietal denomination of the new variety is "PSI-R86.745", botanically known as *Rubus idaeus*, and is sometimes hereinafter referred to as '745. The new variety resulted from a breeding program with the goal to develop new and distinct raspberry varieties.

The following characteristics and particularly distinguishing and outstanding in the new variety:

1. everbearing fruiting habit, fruits on first year primocanes;
2. reduced thorns, i.e., virtually thornless;
3. large sized, golden colored fruit having good flavor; and
4. vigorous, tall, non-branched primocanes with a distinct color contrast between the mature primocane foliage and immature sucker foliage.

BRIEF DESCRIPTION OF THE ILLUSTRATIONS

The accompanying photographs show typical specimens of the new variety at various stages of development:

DESCRIPTION OF THE NEW VARIETY

I. Fruit Production Characteristics

Figure 1:
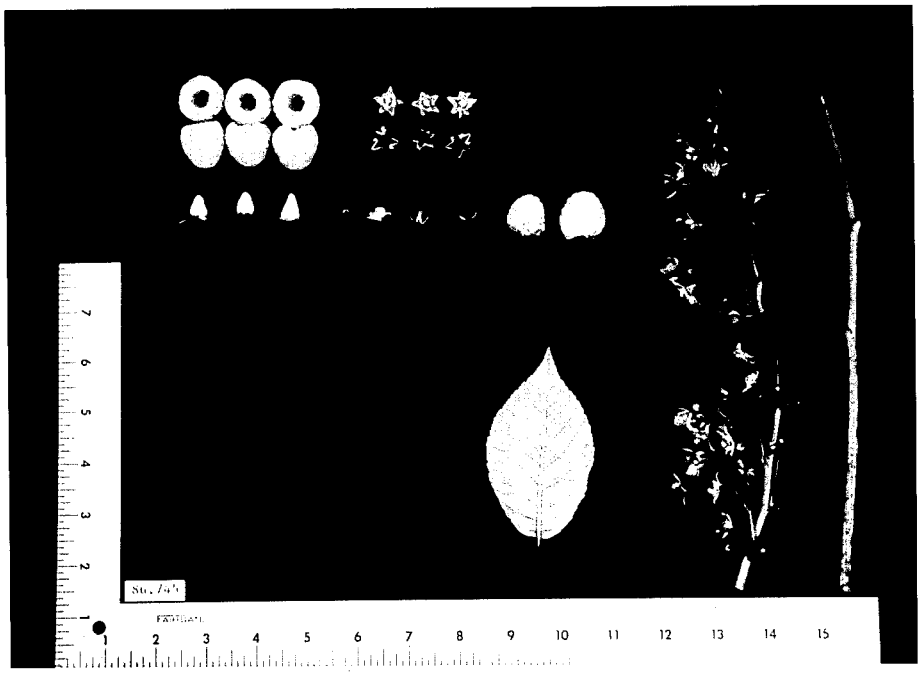
FIG. 1 shows typical plant parts of the new variety including leaves, (both upper and lower surfaces of a mature leaf and the upper surface of an immature leaf), individual flowers, inflorescences, mature fruit, primocane, receptacle, and the developmental stages of the fruit from flower to maturity.
Figure 2:
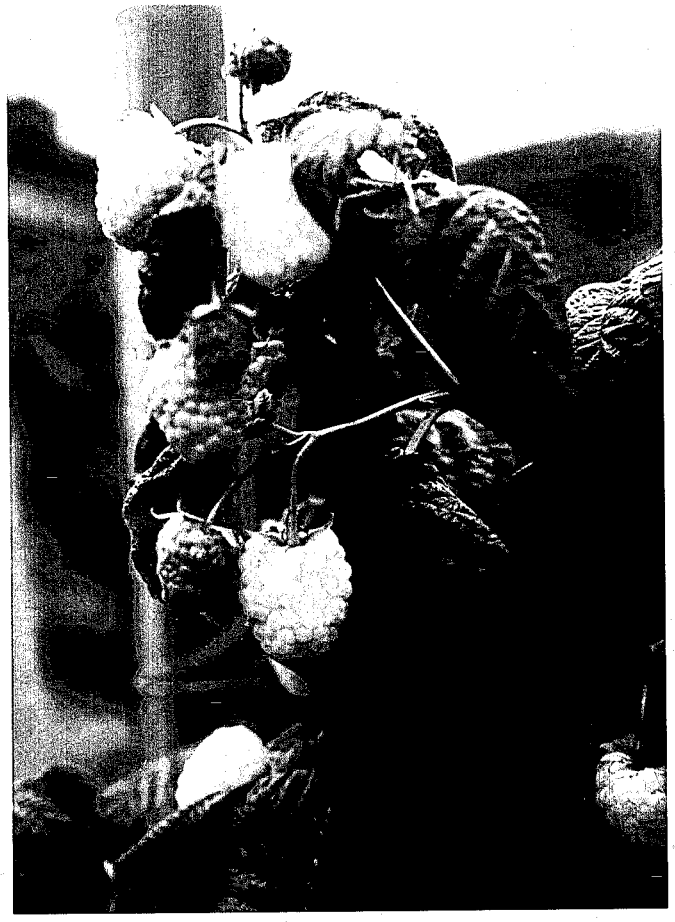
FIG. 2 depicts a typical fruiting terminal showing the exposure of the fruit, and notably evident twisting of the foliage as well as the coarse texture of the fruit and exposure of the druplets.
Figure 3:
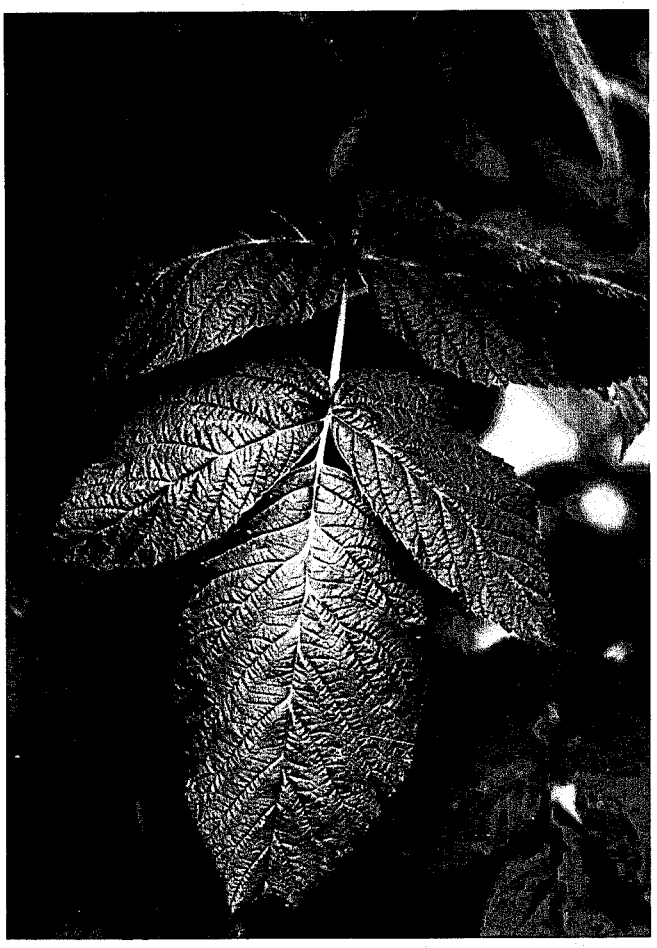
FIG. 3 shows a typical five-foliate mature leaf with its reduced corrugations, somewhat flat surface and long slender appearance.
Figure 4:
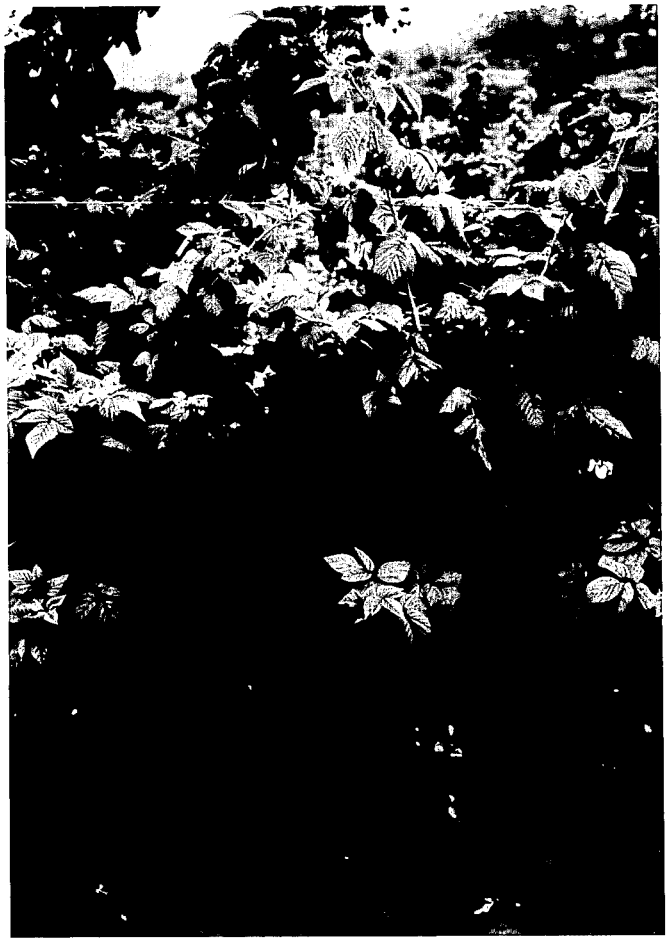
FIG. 4 shows typical plant growth and fruiting characteristics in mid-August, the photograph showing the tall non-branched primocanes, good sucker vigor, and distinct color contrast between the mature primocane foliage and immature sucker foliage.

The new variety is primarily adapted to the climate and growing conditions of the central coast of California, where it was selected and tested. This region provides the necessary winter temperatures required for it to produce a strong vigorous plant and remain in fruit production from August through November and May through July. The nearby Pacific ocean provides cool temperatures needed to maintain fruit quality during the fall and spring production months.

Initial yield studies have shown that '745 is capable of producing moderate yields, considerably less than the commercially grown red raspberry variety "Heritage" during the fall months, and much greater yields than the commercially grown red raspberry variety "Willamette" during the spring months, with a season average fruit size considerably larger than either variety. '745 produces approximately one third of its total yield during the fall months (August through November) peaking during the second and third weeks of September, with two thirds during the spring months (May through July) peaking during the last week of June and first week of July.

II. Varietal Description

The following is a detailed description of my new variety based on observations taken in August from canes that were planted in January in Watsonville, Calif. Color terminology is in accordance with the Munsell Book of Colors, Munsell Color, Baltimore, Md. (1976).

The described characteristics of the new variety may vary slightly in detail depending upon weather, soil, location and evaluation date. The phenotype may also vary with variations in environments such as, temperature, light, intensity and day length. '745 has not been observed under all possible environmental conditions.

Golden raspberries are not considered a standard commercially grown cultivar on the central coast of California as yet. Nontheless, general comparisons will be made to a commonly known golden raspberry variety "Fall Gold".

Parentage: '745 is a result from a cross of "Heritage"×"PSI.R86.138A", an unnamed, unpatented seedling.

Fruit: Fruit is golden in color at maturity, color near 2.5Y 8.5/8, and characteristically rounded in shape with a few being slightly more conical. Primary fruit is large, averaging up to 6.0 to 6.5 grams in weight. Season average fruit size (3.8 grams) is nearly twice as large as "Fall Gold". Fruit size is slightly larger during the fall months as compared to the spring. The fruit cavity is large, averaging 18.7 millimeters (mm) deep×11.0 mm wide and funnel shaped. Druplets are medium in size, averaging 100 to 120 per primary berry, typically fewer per secondary and tertiary berries. Druplets are positioned strongly exerted from the berry. This tends to give the fruit a coarse texture as compared to "Fall Gold". Receptacle is typically large, (14.8 mm long×8.3 mm wide) and cone shaped tapering to a blunt tip. Seeds are medium in size averaging 1.4 to 1.8 milligrams (mg) in weight from the primary berry. The calyx consists of an average at 5 to 6 sepals, more commonly 6 and acuminate in shape. The fruit is moderately firm, separating easily form the large receptacle, and with very good flavor. Fruit is susceptible to botrytis fruit rot during rainy periods and is typically less firm than "Heritage".

Plant: '745 is capable of producing a vigorously tall plant (1.9 meters), as compared to the shorter "Fall Gold". Primocanes are non-branched and large, with a basal diameter averaging 1.5–1.7 centimeters (cm). '745 suckers freely with a distinct color contrast between mature primocane foliage, color near 5GY ¾ and immature sucker foliage, color near 5GY ⅝. The primocane produces many laterals on the upper 30–40 percent of the cane. Laterals can average up to 20–30 cm in length. The yellowish-green primocane, color near 2.5GY 6/4, is virtually thornless having very few prickles with an average length of 0.3 mm to 0.5 mm at mid-cane as compared to "Fall Gold" which has slightly more prickles that are much longer and very stout. Thorns are nearly the same color as the primocane with a dull reddish tip, color near 5R 3/6. Second year floricanes, color near 5YR 4/6 produce many laterals down the length of the cane with a lot of fruit, giving good production in June and July.

Foliage: Leaf characteristics are compared to those of "Fall Gold" in Table 1. All leaf characteristics and measurements are taken from a three-foliate leaf.

TABLE 1

Comparison of leaf characteristics of '745 and "Fall Gold" from plants grown in Watsonville, California during mid-August.

| CHARACTER | '745' | "FALL GOLD" |
|---|---|---|
| Leaf Color (upper surface) | 5GY ¾ | 5GY ¾ |
| Terminal Leaflet (three foliate) Size - l × w (cm) | 14.2 × 10.8 | 9.0 × 8.5 |
| Terminal Leaflet (three foliate) Ratio (L/W) | 1.3 | 1.1 |

Mature leaves are medium yellow-green, similar to "Fall Gold". Petioles are long (average 7.0 cm) and large in diameter (averaging 3.5 mm). Petiole texture is smooth, without prickles, unlike "Fall Gold" which has few but very stout prickles. Petioulule length averages 4.0 cm. Mature terminal leaflets at approximately mid-cane are considerably larger than those of "Fall Gold" as shown by the length×width measurements, yet less rounded than "Fall Gold" as describes by the ratio of length/width. Foliage has nearly an equal number of three-foliates and five-foliates. Occasionally the terminal leaflet of a three-foliate will develop points to true independent leaflets. The terminal leaflet is cordate in shape tapering to an acuminate point. Surface is light to moderately rugose at mid-cane, considerably smoother than "Fall Gold", becoming strongly rugose toward the upper portion of the primocane. Foliage is primarily flat in appearance occasionally with a slight twist at mid-cane becoming more irregular with notable marked twisting towards the upper portion of the primocane.

*Isozymes in leaf extract.*—Studies of protein polymorphism in Rubus by the starch gel electrophoresis method were carried out to characterize this newly developed variety and distinguish it from other varieties.

Isozymes were extracted from young leaves and characterized using starch gel electrophoresis techniques. The following isozymes were characterized: triose phosphate isomerase (TPI: EC 5. 3. 1. 1); phosphoglucoisomerase (PGI: EC 5. 3. 1. 9) and phosphoglucomutase (PGM: EC 2. 7. 5. 1).

The plant material used was both field and greenhouse grown in Watsonville, Calif. Newly matured leaves (0.5 g fresh weight) from the growing tips of canes were used. Samples were held at 4–8 C and analyzed within 24 hours of collection.

The tris extraction buffer (pH 8.0) was as follows: 0.05M tris base, 0.007M citric acid (monohydrate), 0.1% cysteine hydrochloride, 0.1% ascorbic acid (Na salt or free acid), 1.0% polyethylene glycol, and 80 ul/1 2-mercaptoethanol. Samples were extracted in 10–12 ml cold buffer by homogenizing at 17,000 rpm or by hand grinding.

Gel and electrode buffers for the enzyme systems analyzed are given in Table 2. Electrophoresis specifications for these enzyme systems are given in Table 3.

The starch gel was prepared and held overnight at 20C ±5C prior to use. To form the starch gel, potato starch (30 g) is dissolved in 80 ml of cold gel buffer (System A: gel buffer 50 ml/electrode buffer 30 ml) in a vacuum flask (1.0 l). Boiling gel buffer (220 ml) is added to the starch solution. Starch is completely dissolved by vigorously swirling the solution in the vacuum flask, and vacuumed for 15 to 30 seconds. The gel solution is immediately poured onto a 20.5 cm×22.0 cm plexiglass gel plate and covered until use.

Samples are inoculated onto paper wicks and placed in a cooled gel (4C); covered with Saran and electrophoresed for 20 minutes. The wicks are removed and the system is run until the dye front travels approximately 5–8 cm.

Following electrophoresis, the gel is sliced and stained for each enzyme system. Banding patterns are interpreted as they develop and gel slices are fixed in 50% glycerol.

TABLE 2

| SYSTEM | pH | GEL BUFFER | G/L | ELECTRODE BUFFER | G/L | pH |
|---|---|---|---|---|---|---|
| A | 8.3 | Tris Base | 65.0 | Lithium Hydroxide | 1.2 | 8.3 |
| | | Citric Acid (Monoh) | 1.5 | Boric Acid | 12.0 | |
| B | 7.0 | DL-Histidine HCL (Monohydrate) | 1.2 | Tris Base | 16.5 | 7.0 |
| | | | | Citric Acid (Monoh.) | 9.0 | |
| C | 7.8 | Tris Ultra Pure | 1.09 | Tris Ultra Pure | 16.35 | 7.8 |
| | | Citric Acid | 0.63 | Citric Acid | 9.03 | |
| | | $Na_2$ EDTA | 0.45 | $Na_2$ EDTA | 0.45 | |

TABLE 3

| RUBUS ELECTROPHORESIS SPECIFICATIONS | | | | |
|---|---|---|---|---|
| SYSTEM | ENZYME | pH | CURRENT | GEL SLICE |
| A | PGI | 8.3 | 275 V | 2 |

TABLE 3-continued

| RUBUS ELECTROPHORESIS SPECIFICATIONS | | | | |
|---|---|---|---|---|
| SYSTEM | ENZYME | pH | CURRENT | GEL SLICE |
| B | PGM | 7.0 | 150 V | 3 |
| C | TPI | 7.8 | 50 mA | 2 |

The isozyme banding patterns of '745 for the three enzyme systems compared to those of "Fall Gold" are shown below. The RF value is the ratio between the distance (cm) traveled by the band to the distance traveled by the dye front (cm).

Figure 5:
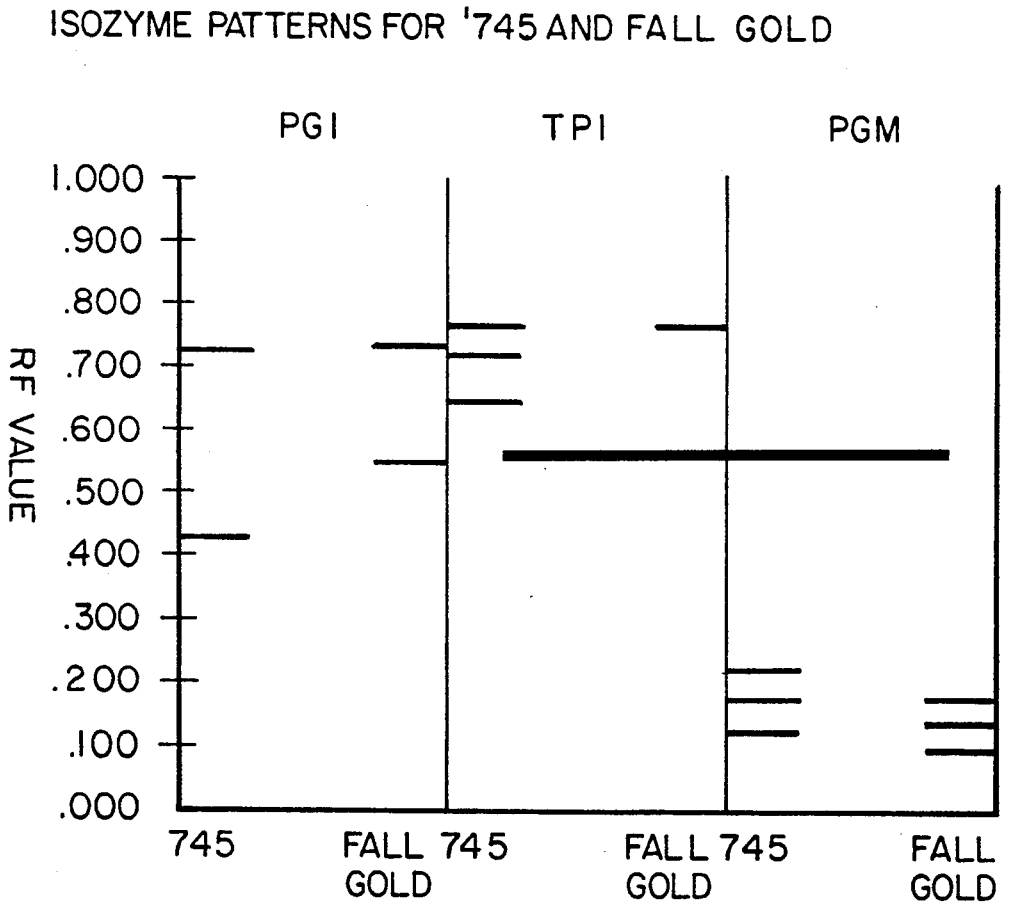
FIG. 5 shows isozyme patterns for the varieties '745 and 'Fall Gold'.

The patterns for PGI and PGM are similar for both '745 and "Fall Gold", but vary in average RF value. The TPI isozyme pattern for '745 is distinctly different from "Fall Gold". The combination of isozyme patterns shown in FIG. 5, derived from the specific techniques described, support '745 as a unique raspberry variety.

Inflorescence: Inflorescences are borne in cymose clusters with an average of 6 to 8 berries per terminal prior to the first three-foliate. The fruit borne on the terminals and short laterals on the upper portion of the primocane may be slightly concealed beneath the twisting and cupping foliar canopy, while fruit on the longer laterals is more easily accessible. Laterals are strong and hold up well under the large fruit size. Flowers are medium in size and produce ample pollen for good pollination. Flowers consist of an average of 5 to 6 obovate petals per flower, more commonly 6.

III. Insect and Disease Resistance

The new variety may not be resistant to any of the known insect and disease pests common in Californa. It is known to be moderately susceptible to the two-spotted spider mite, powdery mildew and yellow rust. It is also known to be particularly susceptible to Botrytis fruit rot during rainy periods. It has not been tested for susceptibility to Phytophthora root rot or any of the virus complexes.

I claim:

1. A new and distinct golden raspberry variety, substantially as shown and described.

* * * * *